(12) United States Patent
Kwok et al.

(10) Patent No.: US 9,707,367 B2
(45) Date of Patent: Jul. 18, 2017

(54) AUTO-ADJUSTING MASK STABILIZER

(75) Inventors: Philip Rodney Kwok, Chatswood (AU); Enrico Brambilla, Drummoyne (AU); Gregory Robert Peake, Kingsford (AU); Robert Edward Henry, Roseville (AU); Lee James Veliss, West Ryde (AU); Philip John Gunning, North Rocks (AU)

(73) Assignee: ResMed Limited, Bella Vista (AU)

( * ) Notice: Subject to any disclaimer, the term of this patent is extended or adjusted under 35 U.S.C. 154(b) by 2172 days.

(21) Appl. No.: 12/134,871

(22) Filed: Jun. 6, 2008

(65) Prior Publication Data

US 2008/0314390 A1   Dec. 25, 2008

Related U.S. Application Data

(60) Provisional application No. 60/945,380, filed on Jun. 21, 2007.

(51) Int. Cl.
*A61M 16/06* (2006.01)

(52) U.S. Cl.
CPC .... *A61M 16/0683* (2013.01); *A61M 16/0616* (2014.02); *A61M 16/0622* (2014.02); *A61M 16/0638* (2014.02); *A61M 16/06* (2013.01); *A61M 16/0655* (2014.02)

(58) Field of Classification Search
CPC .............. A61M 16/06; A61M 16/0616; A61M 16/0622; A61M 16/0638; A61M 16/0683; A61M 16/0633; A61M 16/0644; A61M 16/0655
USPC ............ 128/206.24, 207.11, 206.21, 205.25, 128/206.23, 206.28, 202.27, 206.22, 128/206.25, 206.26, 203.27, 206.29, 128/207.12, 207.13
See application file for complete search history.

(56) References Cited

U.S. PATENT DOCUMENTS

| | | | |
|---|---|---|---|
| 2,984,726 A * | 5/1961 | Roeser ...................... 200/302.2 |
| 4,083,065 A * | 4/1978 | Warncke .......................... 2/424 |
| 4,782,832 A | 11/1988 | Trimble et al. |
| 5,243,971 A | 9/1993 | Sullivan et al. |

(Continued)

FOREIGN PATENT DOCUMENTS

| | | |
|---|---|---|
| DE | 102010021276 A1 * | 11/2010 |
| EP | 0 526 824 A2 | 2/1993 |

(Continued)

OTHER PUBLICATIONS

Photographs of Weinmann Mask, acquired prior to 1998 (3 pages).

(Continued)

*Primary Examiner* — Bradley Philips
(74) *Attorney, Agent, or Firm* — Nixon & Vanderhye P.C.

(57) ABSTRACT

A forehead support for a facial mask is adapted to be moveable between a first position with respect to a frame of the mask and a second position with respect to the frame. The forehead support includes a biasing mechanism that urges the forehead support in the second position. A method of positioning a forehead support with respect to a frame of a patient interface includes positioning the forehead support and patient interface assembly on a face; disengaging a forehead support locking mechanism; allowing the forehead support to move from a first position to a second position; and engaging a forehead support locking mechanism.

59 Claims, 7 Drawing Sheets

(56) References Cited

U.S. PATENT DOCUMENTS

| | | | |
|---|---|---|---|
| 5,245,995 A | 9/1993 | Sullivan et al. | |
| 6,520,182 B1* | 2/2003 | Gunaratnam | |
| 6,532,961 B1* | 3/2003 | Kwok et al. | 128/206.21 |
| 6,973,929 B2 | 12/2005 | Gunaratnam | |
| 7,971,590 B2* | 7/2011 | Frater et al. | 128/206.24 |
| 7,975,692 B2* | 7/2011 | Eifler et al. | 128/205.25 |
| 2004/0099272 A1 | 5/2004 | Kwok et al. | |
| 2005/0072428 A1* | 4/2005 | Ho et al. | 128/205.25 |
| 2005/0155603 A1* | 7/2005 | Frerichs et al. | 128/206.21 |
| 2006/0289010 A1 | 12/2006 | Kwok et al. | |
| 2007/0017525 A1* | 1/2007 | Madaus et al. | 128/207.11 |
| 2007/0062537 A1* | 3/2007 | Chiesa et al. | 128/207.11 |
| 2008/0264422 A1* | 10/2008 | Fishman | 128/207.11 |
| 2011/0094516 A1 | 4/2011 | Chang | |

FOREIGN PATENT DOCUMENTS

| | | |
|---|---|---|
| WO | WO 98/05374 | 2/1998 |
| WO | WO 2006/074517 A1 | 7/2006 |
| WO | WO 2007/143793 A1 | 12/2007 |

OTHER PUBLICATIONS

New Zealand Examination Report dated Jun. 24, 2008 in corresponding New Zealand Application No. 569187.
Extended European Search Report mailed Feb. 17, 2009 in European Appln. No. 08158797.4.
Extended European Search Report dated Dec. 22, 2014 issued in European Application No. 14169108.9 (8 pages).

* cited by examiner

AUTO-ADJUSTING MASK STABILIZER

CROSS REFERENCE TO RELATED APPLICATION

This application claims priority to U.S. Provisional Application 60/945,380, filed Jun. 21, 2007, the entire contents being incorporated herein by reference.

FIELD OF THE INVENTION

Sample embodiments of the present invention relates to an automatically adjusting mask stabilizer for a facial mask used to supply breathable gas to a wearer's airways.

Sample embodiments of the invention have been developed primarily for use in supporting a mask used in Continuous Positive Airway Pressure (CPAP) treatment of, for example, Obstructive Sleep Apnea (OSA) and other ventilatory assistance treatments such as Non-Invasive Positive Pressure Ventilation (NIPPV) and will be described hereinafter with reference to this application. However, it will be appreciated that the sample embodiments of the invention are not limited to these particular uses and are also suitable for use with, for example, nasal (nose only), mouth only, or full-face (i.e. nose and mouth) masks, or prongs, nozzles, puffs or the like.

BACKGROUND OF THE INVENTION

CPAP treatment is a common ameliorative treatment for breathing disorders including OSA. CPAP treatment, as described in U.S. Pat. No. 4,944,310, provides pressurized air or other breathable gas to the entrance of a patient's airways at a pressure elevated above atmospheric pressure, typically in the range 4-20 cm $H_2O$.

It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes the pressure can be made to vary in a complex manner throughout the respiratory cycle. For example, the pressure at the mask during inspiration or expiration can be varied through the period of treatment.

Typically, the ventilatory assistance for CPAP or NIPPV treatment is delivered to the patient by way of a nasal mask. Alternatively, a mouth mask or full face mask or nasal prongs can be used. In this specification any reference to a mask is to be understood as incorporating a reference to a nasal mask, mouth mask, full face mask or nasal prongs.

In this specification any reference to CPAP treatment is to be understood as embracing all of the above described forms of ventilatory treatment or assistance.

A CPAP apparatus broadly comprises a flow generator constituted by a continuous source of air or other breathable gas such as a hospital piped supply or a blower. In the latter case, an electric motor drives the blower and is typically controlled by a servo-controller under the control of a microcontroller unit. In either case, the gas supply is connected to a conduit or tube which in turn is connected to a patient nasal or full-face mask which incorporates, or has in close proximity, an exhaust to atmosphere for venting exhaled gases. Examples of prior art nasal masks are shown in U.S. Pat. Nos. 4,782,832 and 5,243,971.

The supply conduit delivers gas into a chamber formed by walls of the mask. The mask is normally secured to the wearer's head by straps. The straps are adjusted to pull the mask against the face with sufficient force to achieve a gas tight seal between the mask and the wearer's face.

A problem that arises with the use of the existing masks is that in order for the straps to be tight, the mask is compressed against the wearer's face and may push unduly hard on the wearer's nose or face. Additionally, the mask may move around the wearer's face. Thus, there has been hitherto provided a stabilizing support, such as a forehead support, which provides a support mechanism between the mask and the forehead. This forehead support prevents both the mask from pushing too strongly against the wearer's nose and/or facial region (by distributing forces) as well as minimizing movement of the mask with the addition of a contact point between the mask and the wearer's head thereby reducing uncomfortable pressure points. Additionally, the forehead support can be arranged to prevent the gas supply conduit from contacting the wearer's forehead or face.

In order to fit a mask system to a patient, the cushion is fitted to the face of the patient and an ideal position is found. The ideal position is one in which a good seal is formed and the mask feels comfortable to the patient. Once the ideal position is found, the forehead support is brought into contact with the patient's head to provide stability to the ideal position of the mask relative to the patient's head.

Another problem that arises with the use of existing masks is that many forehead supports require two hands to adjust. One hand is typically used to secure the mask, while the other hand is used to adjust the position of the forehead support. Such an adjustment may require too high a level of dexterity for some patients or clinicians. In addition, existing mask systems provide discrete adjustment points for the position of the forehead support, leading to a trial and error process in determining the ideal position. It is also difficult to determine how many discrete positions should be provided. If too few discrete positions are provided, it may not be able to set or lock the forehead support in a position that truly stabilizes the mask in the ideal position. If too many discrete positions are provided, the fitting may be complicated by the patient being unable to decide which position stabilizes the mask in the ideal position.

An even further problem with the use of existing masks is that the adjustment of the forehead support changes the inclination between the forehead support pads and the patient's forehead. For example, the forehead support shown in U.S. Pat. No. 6,532,961 includes a frame that is movably (e.g. pivotably) adjustable with respect to the mask. Pivoting of the forehead support during the adjustment process changes the inclination between the pad and the patient's forehead and may result in an undesirable change in the amount of support provided by the forehead support.

Thus, a need has developed in the art to address one or more of the above problems.

SUMMARY OF THE INVENTION

One aspect of the invention relates to an auto-adjusting mask stabilizer that permits automatic and/or semi-automatic adjustment of a stabilizer (e.g., a forehead support or facial support) for a mask with a minimal level of dexterity and in a shorter amount of time than is currently possible.

Another aspect of the invention relates to an auto-adjusting mask stabilizer that has fewer parts, is less complex, and is of reduced overall dimensions than currently available stabilizers and/or supports.

Still another aspect of the present invention relates to an auto-adjusting mask stabilizer that permits the determination of the ideal mask position, based on comfort and seal, and securement of the ideal position in a shorter amount of time and with less effort than is currently possible.

Yet another aspect of the present invention relates to an auto-adjusting mask stabilizer that may be operated with one hand.

An even further aspect of the present invention relates to an auto-adjusting mask stabilizer that maintains an angle of inclination between the stabilizer and the patient's forehead regardless of the relative position of the stabilizer to the mask.

Another aspect of the present invention relates to an auto-adjusting mask stabilizer that permits the mask stabilizer to be locked in a plurality of positions, including in continuously variable positions.

According to one embodiment of the invention, a forehead support for a facial mask is provided. The mask includes a frame, and the forehead support is adapted to be moveable between a first position with respect to the frame and a second position with respect to the frame. The forehead support comprises a biasing mechanism that urges the forehead support in the second position.

According to another embodiment of the invention, a mask assembly comprises a frame, a forehead support, and a spring mechanism. The forehead support is free to move between a first position and a second position and the spring mechanism is arranged to direct the forehead support to the second position.

According to still another embodiment of the invention, a stabilizer for a patient interface is provided. The patient interface includes a frame, and the stabilizer is adapted to be moveable between a first position with respect to the frame and a second position with respect to the frame. The stabilizer comprises a biasing mechanism that urges the stabilizer into the second position.

According to a further embodiment of the invention, a method of positioning a forehead support with respect to a frame of a patient interface is provided. The method comprises (i) positioning the forehead support and patient interface assembly on a face; (ii) disengaging a forehead support locking mechanism; (iii) allowing the forehead support to move from a first position to a second position; and (iv) engaging a forehead support locking mechanism.

According to yet another embodiment of the invention, a mask assembly comprises a mask frame; a cushion attached to the frame and adapted to contact the face of a patient in a substantially airtight manner; and a stabilizer element connected to and translatably movable with respect to the mask frame. An inclination angle between the stabilizer element and the mask frame remains constant as the stabilizer translates with respect to the frame.

According to an even further embodiment of the invention, a method of fitting a mask assembly to a patient's face is provided. The mask assembly comprises a mask frame, a cushion attached to the mask frame, a stabilizer element supported by the mask frame for translation with respect to the mask frame, a biasing element that biases the stabilizer element with respect to the mask frame, and a lock mechanism that locks the stabilizer element at a position relative to the mask frame against the bias of the biasing element. The method comprises placing the cushion against the patient's face to establish a substantially airtight seal at a first comfortable position; unlocking the lock mechanism to permit the biasing element to bias the stabilizer element against the patient's face when the cushion is in the first comfortable position; and locking the lock mechanism to lock the stabilizer element and stabilize the cushion at the first comfortable position.

According to another embodiment of the invention, a stabilizer for a mask assembly comprises a mask frame extension adapted to be connected to a mask frame of the mask assembly; a pad support element translatably supported by the mask frame extension, the pad support element being configured to support a pad that, in use, contacts a face, e.g. cheeks or upper lip, of a wearer of the mask assembly; and a biasing element that biases the stabilizer with respect to the mask frame extension.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

First Embodiment

Figure 1:
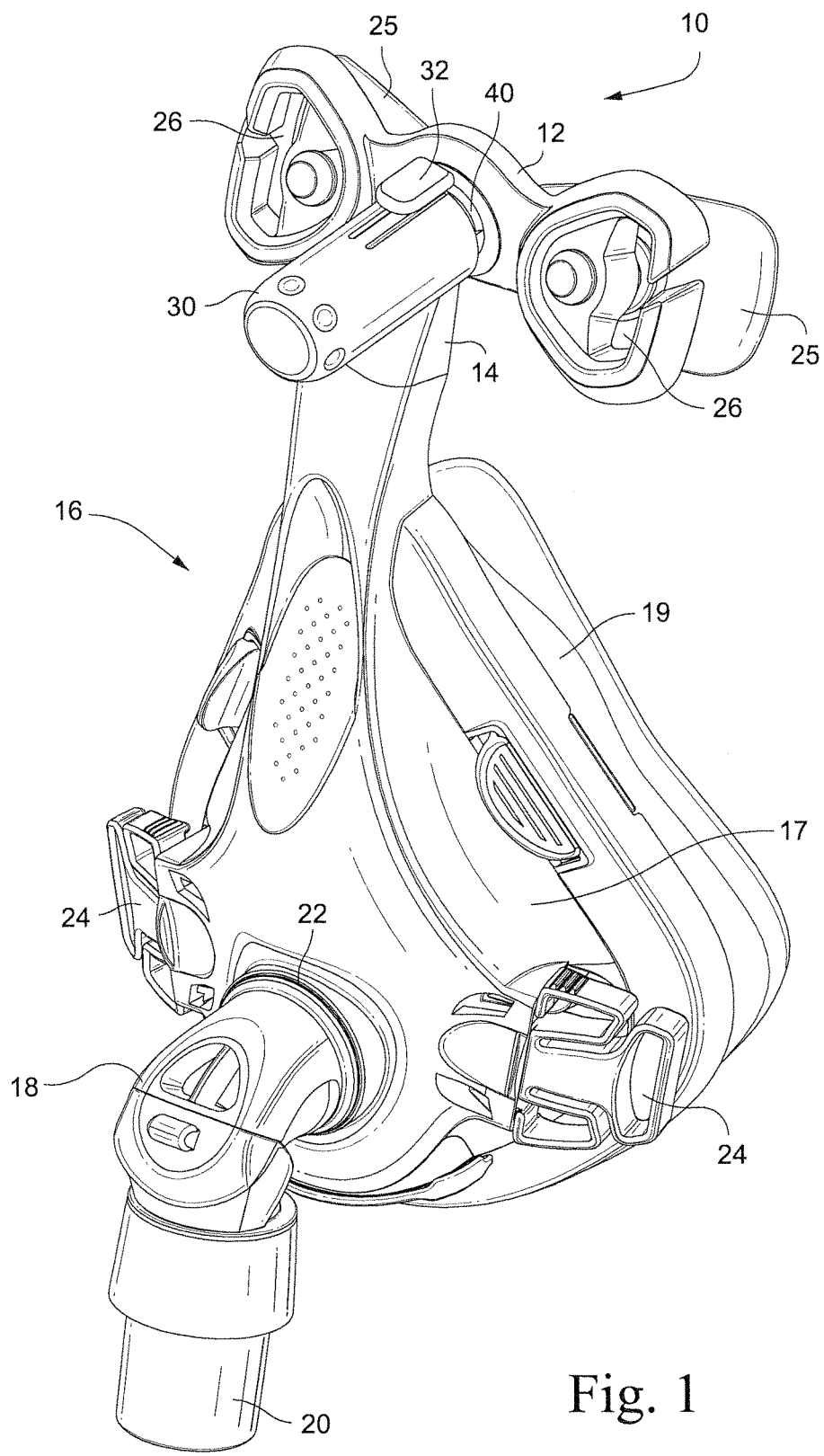
FIG. 1 is a perspective view of a mask including an auto-adjusting mask stabilizer according to one embodiment of the invention.

Referring to FIG. 1, an auto-adjusting mask stabilizer, e.g., forehead support, 10 according to one embodiment of the invention includes a cushion frame 12 mounted to a frame extension 14. The frame extension 14 is connected to, or formed integrally with, a mask 16 used to supply breathable gas to a patient. A separate frame extension allows the auto-adjusting mask stabilizer of the present invention to be adapted to existing mask frames.

The mask 16 includes a mask frame 17 and a mask cushion 19. The mask frame 17 includes an angled connector 18 (e.g., in the form of a swivel elbow) which has a distal end 20 for connection to a gas supply hose (not shown) and a proximal end 22 for connection to the mask 16. The connector 18 communicates the supplied gas from the gas supply hose to the interior of the mask 16. The mask frame 17 also includes a pair of slotted connectors 24 to which are respectively connected ends of a lower head strap (not shown) for securing the mask 16 to the patient's head.

The frame extension 14 is provided on top of the mask frame 17 generally adjacent and above the patient's nose. It should be appreciated that the mask 16 shown in FIG. 1 is just one example of a respiratory mask that may be supported by the mask stabilizer 10. For example, the mask stabilizer 10 may also be used in supporting a nasal mask, a full-face (i.e. nose and mouth) mask, or nasal prongs, puffs, nozzles or the like.

The mask stabilizer 10 may also be used with facial masks in which the angled connector 18 is incorporated into the mask in the general position of the frame extension 14. In this type of mask, the supplied gas flows through or past the mask stabilizer 10.

The cushion frame 12 includes a pair of cushions (e.g., forehead cushions) 25 mounted at each end of the upper portion of the frame 12 on the side adapted to contact the face of the patient (e.g., the patient's forehead). Examples of cushions 25 include open or closed cell foam, silicone, dual durometer foams, single pads or multiple pads joined together. The cushions 25 may be integrally molded with the cushion frame 12 or attached thereto by clips or adhesives or the like. The cushion frame 12 also includes slotted connectors 26 adjacent each of the cushions 25 to which are respectively connected ends of an upper head strap (not shown) for securing the mask 16, including the mask stabilizer 10, to the patient's head.

Figure 2:
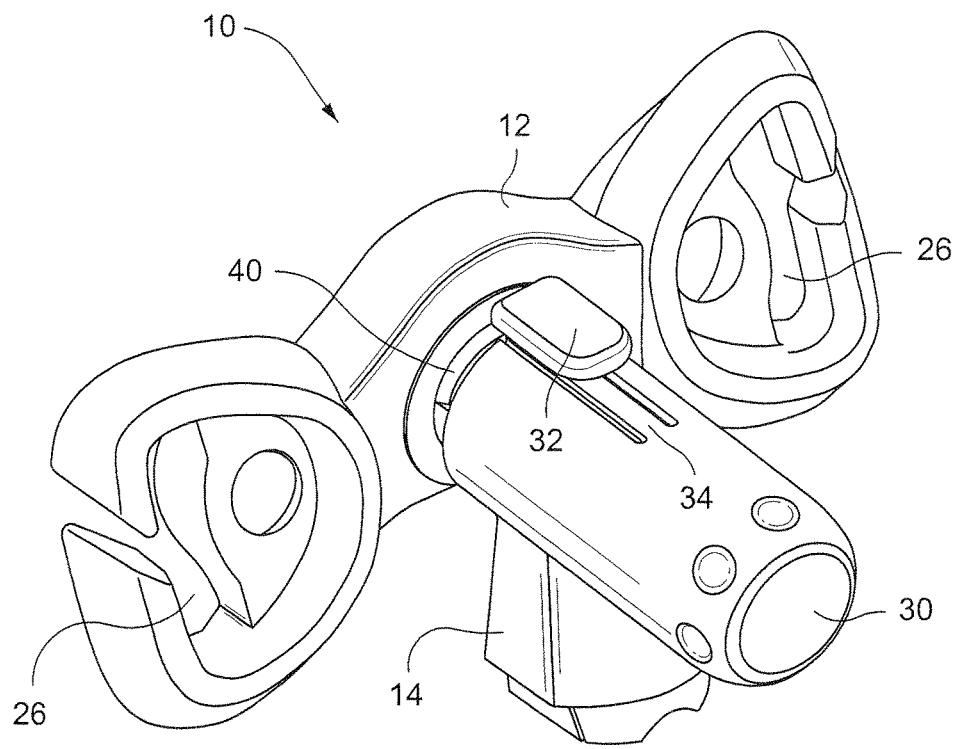
FIG. 2 is a perspective view of an auto-adjusting mask stabilizer of FIG. 1.
Figure 4:
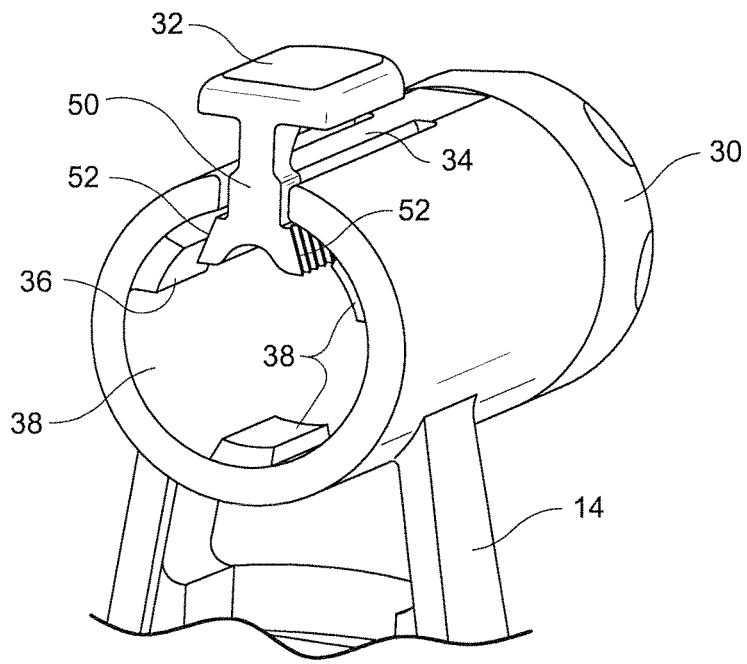
FIG. 4 is a perspective view of a mask extension of an auto-adjusting mask stabilizer of FIG. 1.

Referring to FIGS. 2 and 4, the frame extension 14 includes a frame extension cylinder 30. As shown in FIG. 4, the frame extension cylinder 30 includes a bore 36. A cantilevered lever 34 is formed in an outer peripheral surface of the frame extension cylinder 30. A lock mechanism release button 32 is provided on the free end of the lever 34.

As shown in FIGS. 2 and 4, the cushion frame 12 includes a shaft 40 that is received in the bore 36 of the frame extension cylinder 30.

Figure 3:
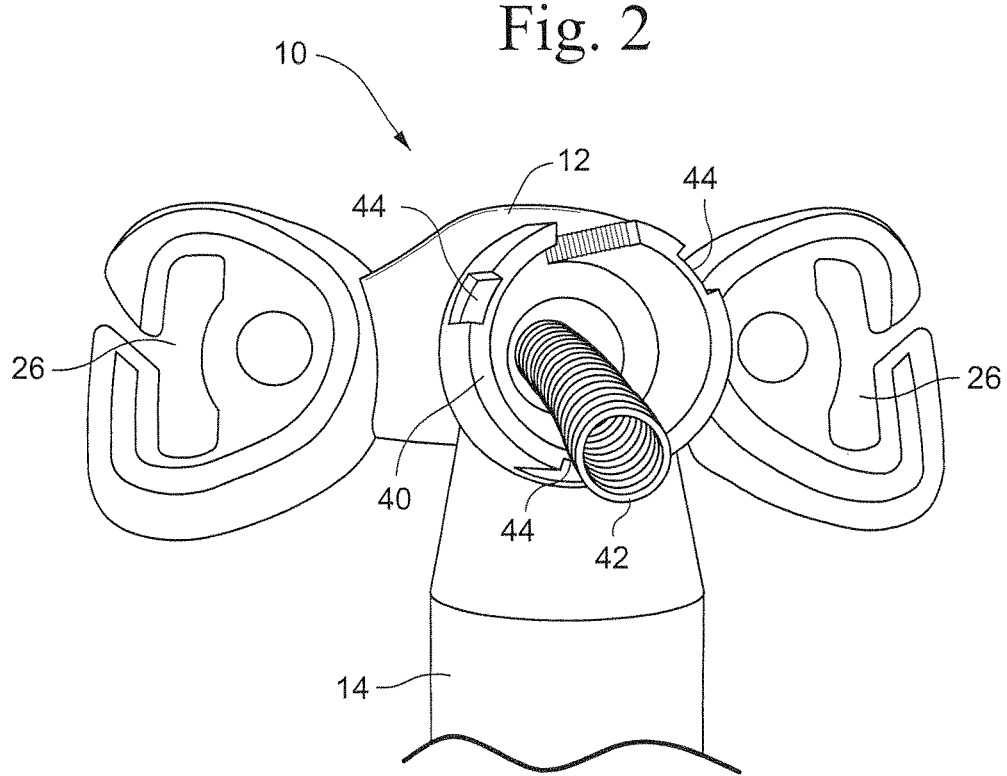
FIG. 3 is a perspective view of a cushion frame of an auto-adjusting mask stabilizer of FIG. 1.

Referring to FIG. 3, the shaft 40 is also in the form of a cylinder. A biasing element 42, e.g. a compression coil spring, is provided inside the shaft 40. The biasing element 42 may be secured to the cushion frame 12 at the end of the shaft, i.e., on the portion of the cushion frame 12 that supports the cushions 25. Referring again to FIG. 1, it should also be appreciated that the mask stabilizer 10 may be adjusted to control the deflection of the mask cushion 19, for example in the region of the patient's nasal bridge.

Figure 5:
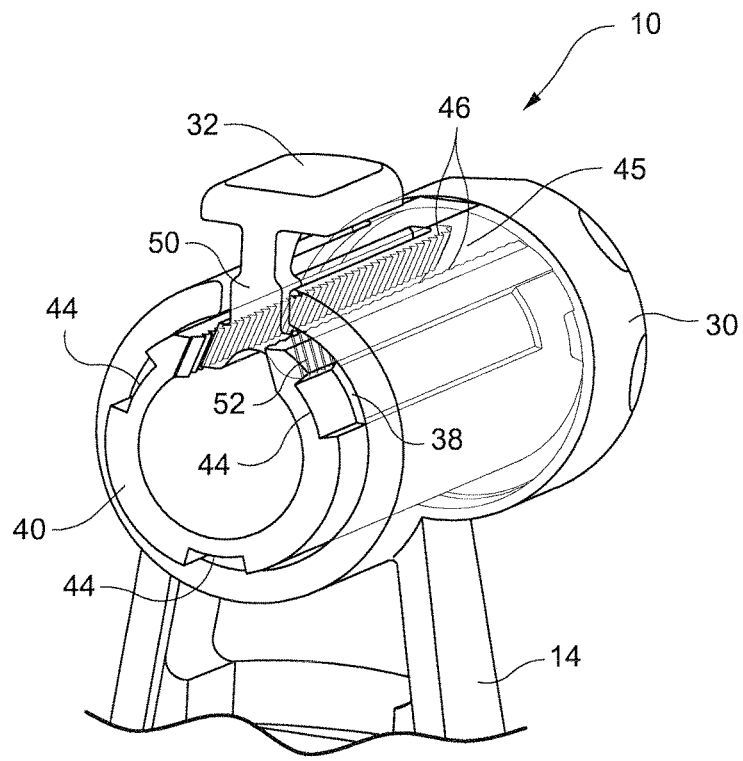
FIG. 5 is a perspective assembly view of the mask extension and cushion frame of the auto-adjusting mask stabilizer of FIG. 1.

Referring to FIG. 4, the frame extension cylinder 30 includes radial projections 38 on the inner cylindrical surface of the cylinder 30. The radial projections 38 extend axially along the cylinder 30. As shown in FIG. 5, the radial projections 38 are received in radial grooves 44 formed in the outer circumferential surface of the shaft 40 of the cushion frame 12. Although the frame extension cylinder 30 and the shaft 40 of the cushion frame 12 are shown having circular cross-sections, it should be appreciated that the cylinder and shaft may have a polygonal cross-section, for example.

As shown in FIG. 4, the lock mechanism release button 32 has a pawl 50 which extends from the release button 32 radially inward of the frame extension cylinder 30. The pawl 50 has ratchet teeth 52 provided on opposite sides. The pawl 50 and the release button 32 are resiliently supported at the end of the cantilevered lever 34.

Referring to FIG. 5, the shaft 40 of the cushion frame 12 includes an axial slot 45. The slot 45 includes ratchet teeth 46 on each side. When the shaft 40 of the cushion frame 12 is inserted into the bore 36 of the frame extension cylinder 30, the pawl 50 of the lock release button 32 is received in the axial slot 45 of the shaft 40 so that the ratchet teeth 52 of the pawl 50 engage the ratchet teeth 46 of the axial slot 45. The engagement of the radial projections 38 of the frame extension cylinder 30 into the radial grooves 44 of the shaft 40 of the cushion frame 12 ensure that the cushion frame 12 and the frame extension cylinder 30 are properly aligned for assembly of the mask stabilizer 10.

The position shown in FIG. 5 is the locked position of the auto-adjusting mask stabilizer 10 and relative movement between the cushion frame 12 and the mask extension 14 is prevented, or locked, by the engagement of the ratchet teeth 52 of the pawl 50 with the ratchet teeth 46 of the slot 45 or by high friction coefficient material on the pawl 50 and/or the ratchet teeth 52 to lock the movement, e.g. a clutch.

The biasing element 42 operates to bias the shaft 40 of the cushion frame 12 away from the cylinder 30 of the frame extension 14. When the lock mechanism is in the position shown in FIG. 5, movement of the cushion frame 12 caused by the biasing force of the biasing element 42 away from the frame extension 14 is prevented by the engagement of the ratchet teeth 52 with the ratchet teeth 46. In order to release the lock mechanism, the release button 32 is pressed downwardly to release the engagement of the ratchet teeth 52 from the ratchet teeth 46. When the ratchet teeth are disengaged, the biasing element 42 biases the cushion frame 12 in a direction away from the frame extension 14 toward the forehead of the patient.

The engagement of the shaft 40 of the cushion frame 12 into the bore 36 of the mask extension cylinder 30 allows the cushion frame 12 to translate with respect to the mask frame 17. Thus, the inclination between the cushion pads 25 and the patient's forehead does not change during adjustment, i.e., movement of the cushion frame 12 with respect to frame extension 14. The mask stabilizer 10 of the present invention thus provides the ability to stabilize the vertical angle of the position of the mask 16 relative to the patient's forehead and also stabilizes the relative set position of the mask 16 throughout the patient's sleep session.

Figure 6:
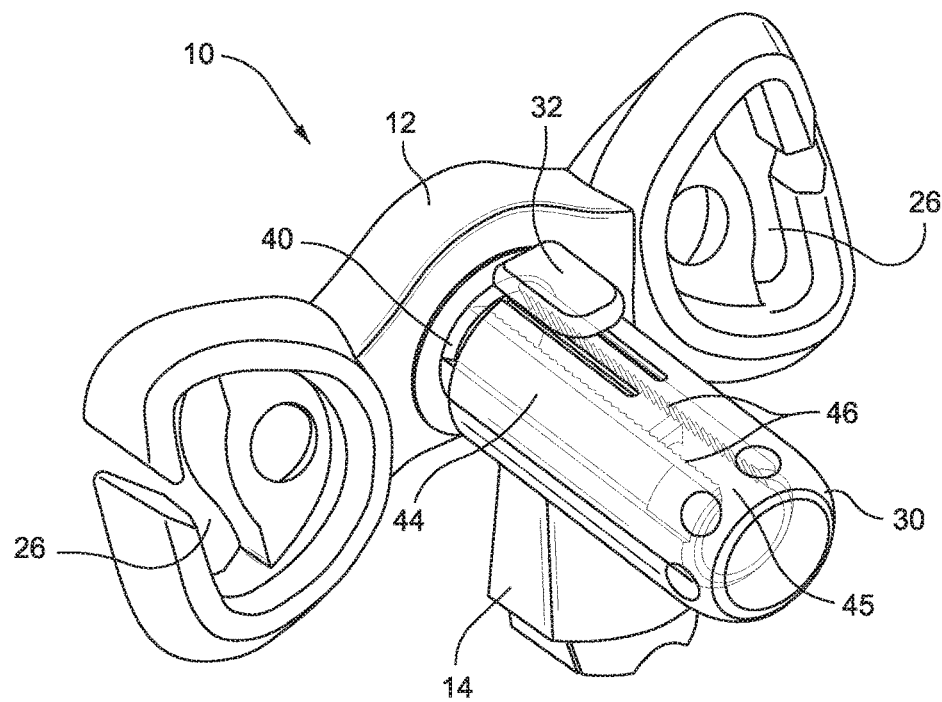
FIG. 6 is a front side perspective view of the mask extension and cushion frame of the auto-adjusting mask stabilizer of FIG. 1.
Figure 7:
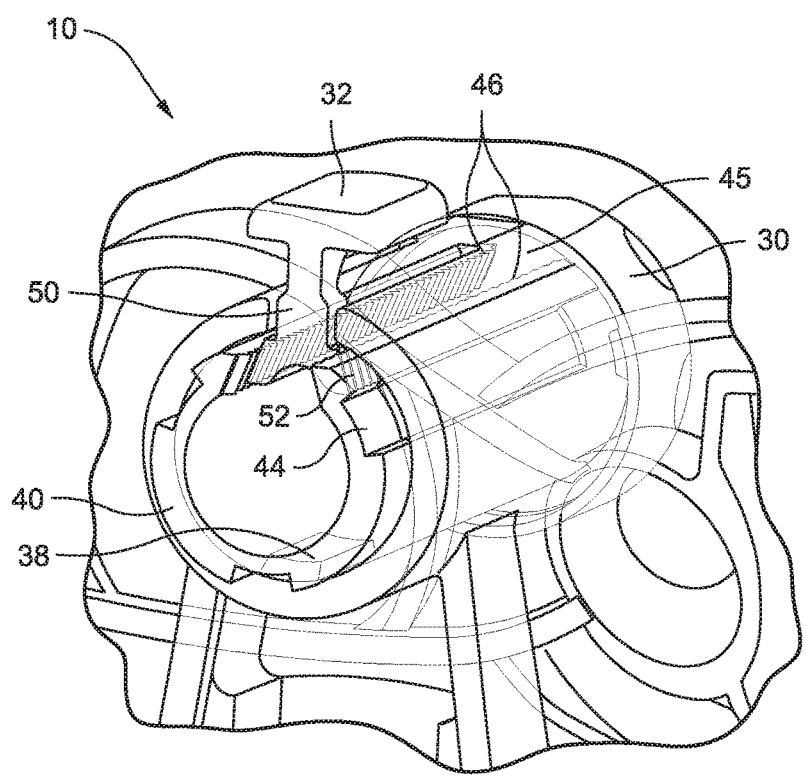
FIG. 7 is a rear side perspective view of the mask extension and cushion frame of the auto-adjusting mask stabilizer of FIG. 1.

Referring to FIG. 6, when the mask system is initially fitted, the shaft 40 of the cushion frame 12 is fully inserted into the mask extension cylinder 30. In this position, the biasing element 42 is under compression and the forehead pads 25 are in the most outward set position so that the compression of the biasing element 42 is at a maximum and the forehead pads 25 are at their closest position to the frame extension 14. In order to determine the ideal position of the mask 16 on the patient's face, the mask 16 is placed in contact with the patient's face and adjusted so that a good seal and comfortable fit are obtained. The lock mechanism release button 32 is then pressed down and the engagement between the ratchet teeth 52 and the ratchet teeth 46 is released. The biasing element 42 then acts to bias the cushion frame 12 toward the patient's forehead and into contact with the patient's forehead. Once the forehead pads 25 are in contact with the patient's forehead, the lock mechanism release button 32 is released and the lock mechanism returns to the locked position (i.e. the ratchet teeth 52 of the pawl 50 return to engagement with the ratchet teeth 46 of the slot 45). Fine tuning of the fit may be achieved by re-pressing the release button 32, which releases the lock mechanism, and moving the mask 16 relative to the patient's face. Once the fine tuning is complete, the release button 32 is again released and the lock mechanism returns to the locked position to lock the cushion frame 12 into position.

The adjustment may be performed with one hand. The patient, or clinic worker, simply presses the release button 32 and adjusts the position of the mask 16 with the same hand used to depress the release button 32. This allows adjustment of the fit of the mask 16 according to the present invention in a quicker manner than mask systems of the prior art. A mask system including the auto-adjusting stabilizer according to the invention may be initially fit in under one second, almost instantaneously, as opposed to up to five seconds as may be required for forehead supports according to the prior art. As the mask adjustment may be performed with one hand, the mask system of the present invention requires less dexterity to adjust than masks of the prior art.

Figure 13:
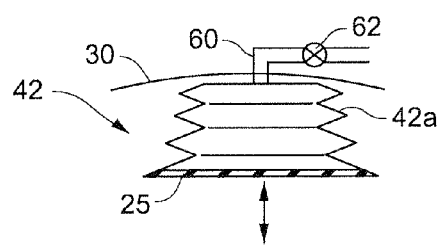
FIG. 13 is an illustration of an auto-adjusting mask stabilizer according to another embodiment of the invention.

As shown in FIG. 3, the biasing element 42 may be a coiled compression spring. For example, the spring could be a stainless steel or nickel-plated spring. It should be appreciated, however, that the biasing element 42 may take other forms. For example, the biasing element 42 may be a compressible open cell foam or silicone rubber elastic band. As another example shown in FIG. 13, the biasing element 42 may be an air spring having a reservoir, or an air bladder or integrally spring-loaded bellows 42a with an elastic memory so as the air is compressed the bladder can stretch and provide a spring force. The air bladder could be in communication with the air being delivered to the mask so that an air line 60 is provided between the inside of the mask frame and the air bladder or bellows 42a so that the air bladder or bellows 42a is under the influence of air pressure which influences or biases the movement of the cushion frame 12 toward the patient's face. It should also be appreciated that the air bladder may be provided with a valve 62 allowing the deflation of the air bladder. In operation, the air bladder or bellows 42a is normally in an extended position. Prior to fitting the mask to the patient, the valve 60 is opened and the air bladder or bellows 42 as is compressed during fitting. The valve 60 is then closed to fix the support in position.

Second Embodiment

Figure 8:
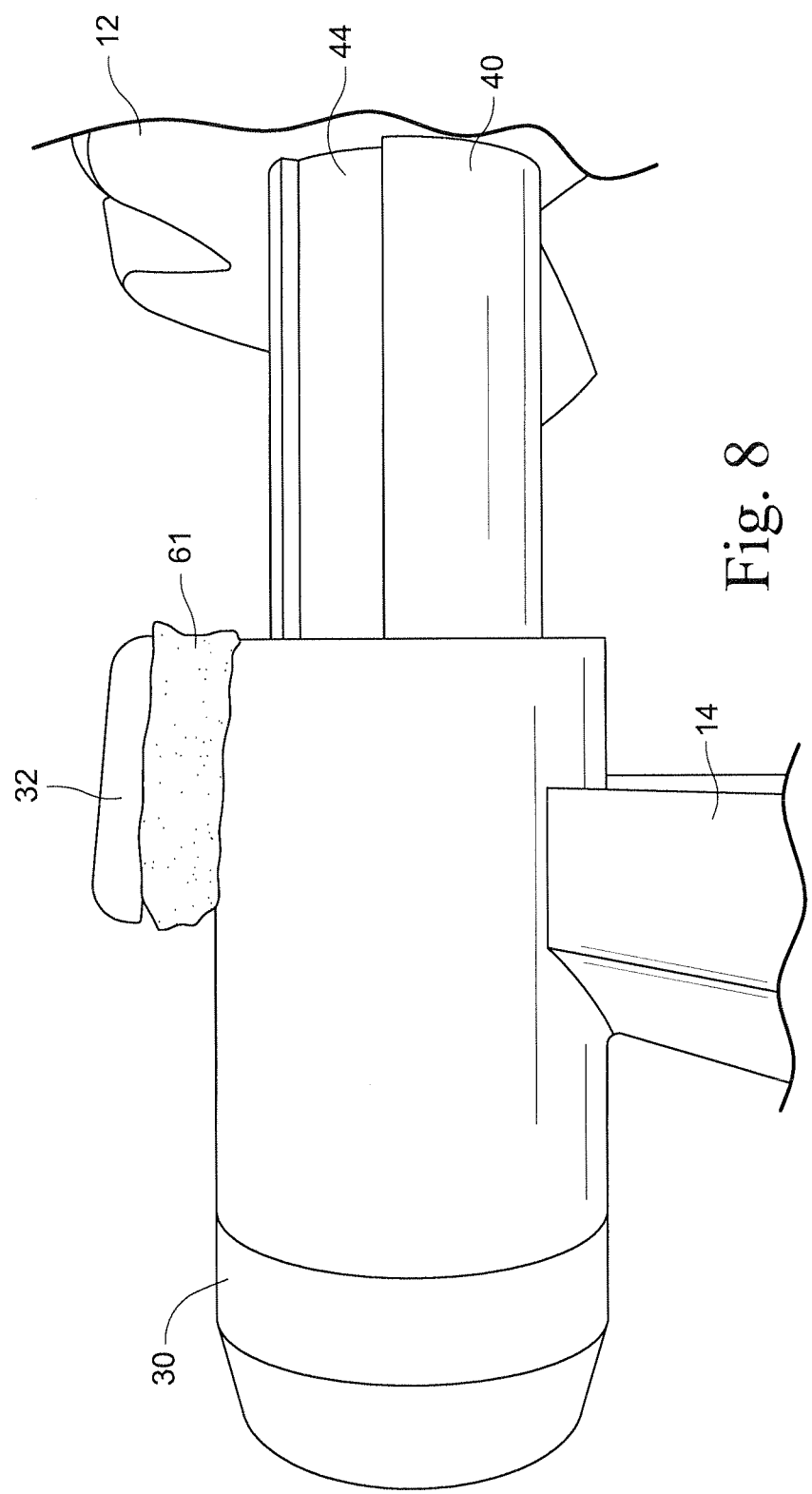
FIG. 8 is a perspective view of an auto-adjusting mask stabilizer according to another embodiment of the invention.

Referring to FIG. 8, according to another embodiment of the invention, a bushing 61 may be provided between the release button 32 and the outer surface of the mask extension cylinder 30. The bushing 61 serves to adjust the force required to depress the release button 32. The bushing 61 may also serve to prevent accidental release of the locking mechanism, for example during movement of the patient during the sleep session. The bushing 61 may also bias the locking mechanism into the locked position.

Alternate Embodiments

Although the lock mechanism release button 32 is shown in the attached drawings as being provided on top of the mask frame extension cylinder 30, it should be appreciated that the release button could also be provided anywhere along the circumference of the mask frame extension cylinder 30, with a corresponding movement of the slot 45 and ratchet teeth 46 of the shaft 40 of the cushion frame 12. It should also be appreciated that the release button could be provided at the closed end of the mask frame extension cylinder 30. However, positioning the release button 32 on top of the frame extension cylinder 30 allows the patient to activate the release button in a natural way and the force that is required to activate the release button is in a plane normal to the direction along which the patient or fitter is positioning the mask. This minimizes the chance of moving the mask while adjusting the position of the cushion frame 12.

Spacing of the ratchet teeth 46 in the slot 45 of the shaft 40 of the cushion frame 12 may be, for example, 1 mm. The position of the cushion frame 12 may thus be adjusted in 1 mm increments. It should be appreciated, however, that other spacings of the ratchet teeth 46 are within the spirit and scope of the invention.

Third Embodiment

Figure 9:
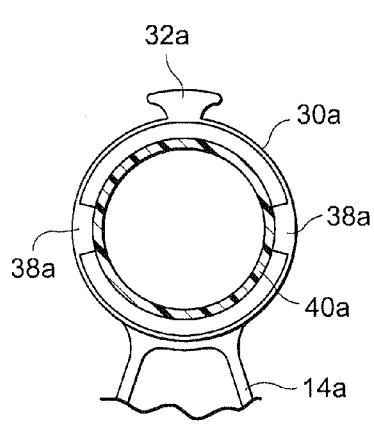
FIG. 9 is an elevation view of an auto-adjusting mask stabilizer according to another embodiment of the invention.

Referring to FIG. 9, an auto-adjusting stabilizer according to another embodiment of the invention includes a frame extension 14a having a frame extension cylinder 30a. A shaft 40a of a cushion frame (not shown) is received in the frame extension cylinder 30a. A biasing element (not shown) is provided between the cylinder 30a and the shaft 40a to bias the shaft 40a relative to the frame 30a.

Radial projections 38a of the frame extension cylinder 30a frictionally engage the outer surface of the shaft 40a to retain the shaft 40a against movement relative to the cylinder 30a caused by the biasing element. A lock mechanism release button 32a is provided for releasing the engagement of the radial projections 38a from the shaft 40a to permit relative movement between the shaft 40a and the cylinder 30a by the biasing element. Depressing the release button 32a causes the cylinder 30a to deform, thus disengaging the projections 38a from the cylinder 40a.

Fourth Embodiment

Figure 10:
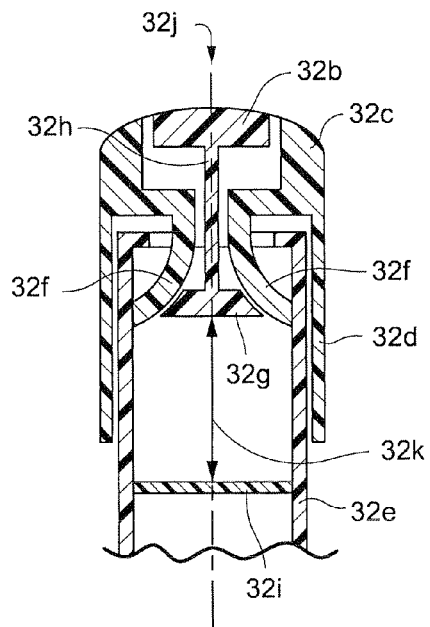
FIG. 10 is an elevation view of an lock release mechanism for the auto-adjusting mask stabilizer of FIG. 9.

As shown in FIG. 10, a lock mechanism 32j according to an embodiment of the invention includes a lock mechanism release button 32b engagable by the patient or clinician. The release button 32b is supported by a release button support 32c. The release button support 32c includes a cylindrical portion 32d that receives a release mechanism sleeve 32e. The sleeve 32e is concentrically supported by the cylindrical portion 32d to permit relative movement between the release button support 32c and the sleeve 32e. Resilient, curved legs 32f couple the support 32c to the sleeve 32e and a cylindrical plug 32g connected to the release button 32b couples the release button 32b to the support 32c. A biasing element 32k, e.g., a spring, is provided between the cylindrical plug 32g and a cross element 32i in the sleeve 32e to bias the lock mechanism 32 into the position shown in FIG. 10. Depressing the release button 32b causes the plug 32g to compress the biasing element 32k. The biasing element 32k is initially compressed by movement of the release button 32b, and then transfers further depression of the release button 32b to the sleeve 32e through engagement of the biasing element and the cross element 32i.

Fifth Embodiment

Figure 11:
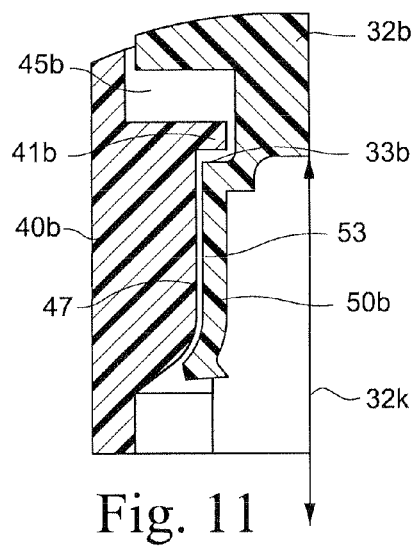
FIGS. 11 and 12 are elevation views of an embodiment of a lock release mechanism for an auto-adjusting mask stabilizer according to the invention.
Figure 12:
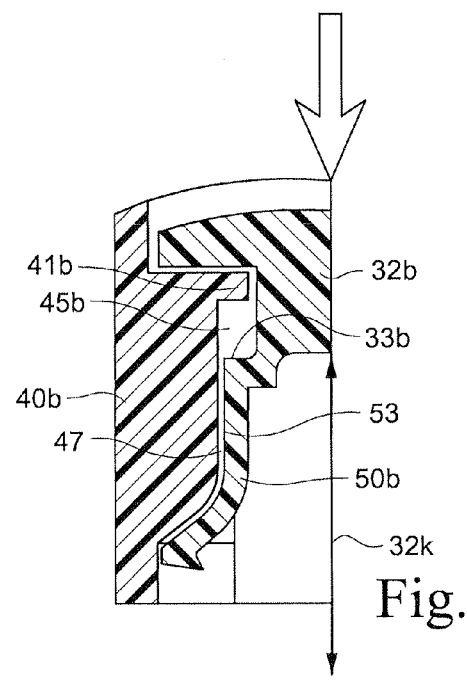

The ratchet teeth of the lock mechanism shown in FIGS. 1-7 may be replaced by a friction lock. Referring to FIGS. 11 and 12, the release button 32b of the lock release mechanism includes a pawl 50b. The pawl 50b includes an engagement surface 53 on each side that engages a corresponding engagement surface 47 of the slot 45b of the shaft 40b of the cushion frame to lock the cushion frame in position. The engagement surfaces 53 of the pawl 50b and the engagement surfaces 47 of the slot 45b may be textured, such as by knurling, to increase the friction between the pawl 50b and the sides of the slot 45b. The use of a friction lock would provide for continuous, or infinite, variability of the position of the cushion frame 12 with respect to the mask 16. In contrast to prior art forehead supports which provide a large number of discrete set points for the support and which may be complicated to use and fit, the provision of an infinite number of set points simplifies using and fitting masks incorporating an auto-adjusting stabilizer according to the invention. Although FIGS. 11 and 12 include a space between the engagement surfaces 47 and 53 for illustrative purposes, it should be appreciated that the surfaces are in contact.

The release button 32b is biased into the locked position shown in FIGS. 11 and 12 by a biasing element 32k, e.g., a spring. A projecting rim 41b in the slot 45b of the shaft 40b engages a shoulder 33b of the release button 32b to maintain the release button 32b in the locked position shown in FIG. 11 When the release button 32b is depressed, as shown in FIG. 12, the amount of engagement between the engagement surfaces 47 and 53 is reduced and the amount of friction is correspondingly reduced. The shaft 40b of the cushion frame is then movable relative to the mask extension cylinder that supports the release button 32b to permit adjustment of the position of the cushion frame.

Sixth Embodiment

Figure 15:
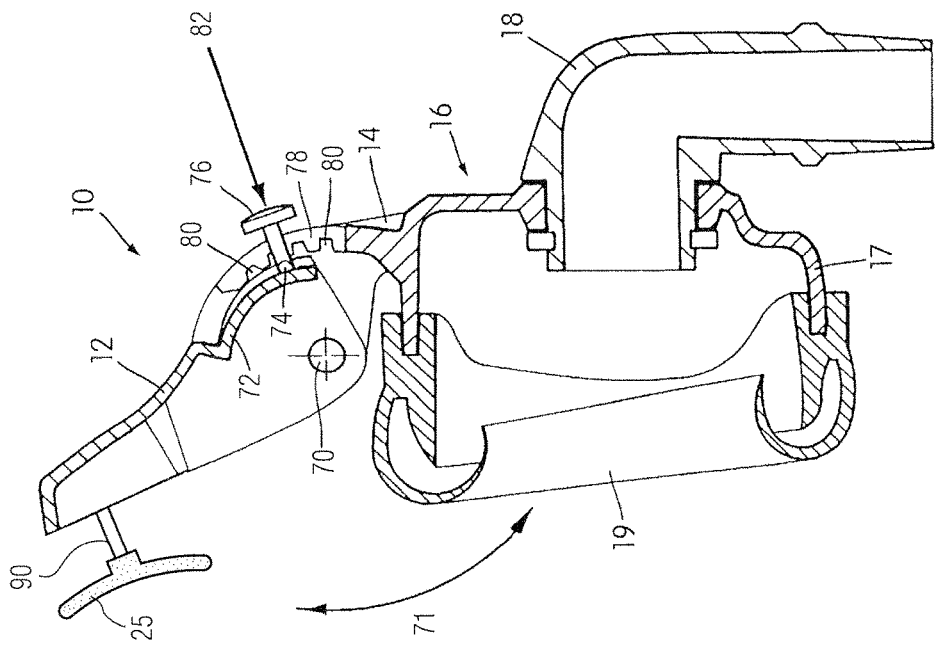
FIGS. 14 and 15 are sectional views of an auto-adjusting mask stabilizer according to another embodiment of the invention.
Figure 14:
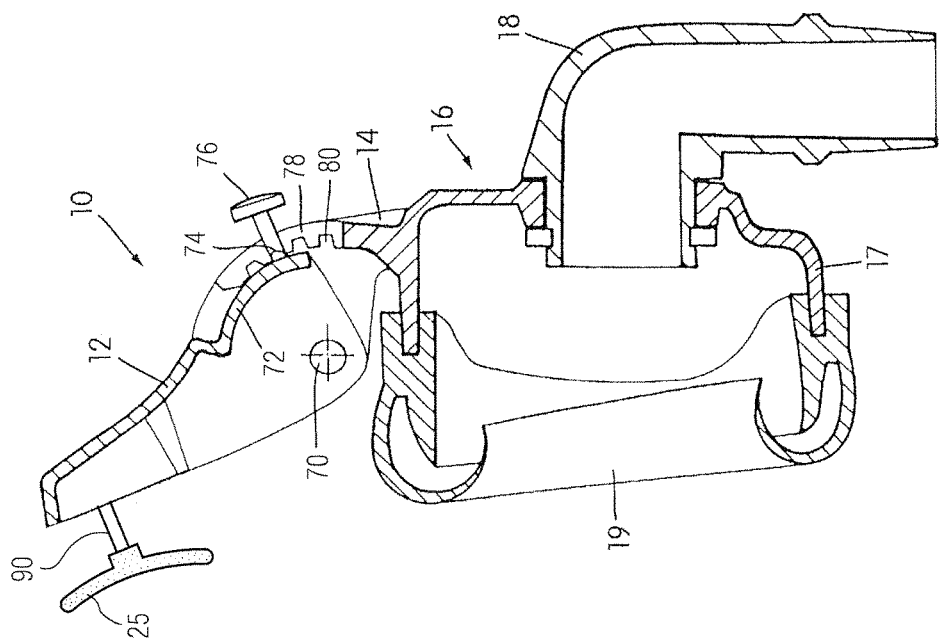

Referring to FIGS. 14 and 15, according to another embodiment, the cushion frame 12 may include a flexible member 72 which has two side by side spaced apart tongues 74 and a middle protruding button 76 on its distal end. The frame extension 14 may include two generally arcuate shaped portions 78 that each have a pair of four grooves 80. It should be appreciated that the pair of four grooves is merely an example and that only two or more grooves are required. It should also be appreciated that the flexible member 72 can be on the frame extension 14 and the grooves 40 can be on the cushion frame 12. The tongue 74 and the grooves 80 extend in a direction substantially parallel to a line extending radially from the axis 70. The cushion frame 12 may be constructed from a plastic material, such as polypropylene or polycarbonate, which allows the member 72 to be flexed relative to the cushion frame 12 upon which is mounted when pressure is applied to the button 76 in the direction of arrow 82. The corresponding movement of the tongues 74 releases them from engagement with one of the pairs of grooves 80 (as shown in FIG. 15) to allow angular adjustment between the cushion frame 12 and the joining member 14 about the axis 30. Releasing the button 76 allows the tongue 74 to resiliently flex back towards the grooves 80. When the tongues 74 and one of the pairs of grooves 80 are aligned (as shown in FIG. 14) the tongues 74 engage one of the pair of grooves 80. When the tongues 74 are engaged with one of the pair of grooves, the cushion frame 12 and joining member 14 are locked against pivotal movement therebetween at a predetermined angle.

A biasing member, such as a torsion spring (not shown), may be provided between the cushion frame 12 and the mask extension 14 to bias the cushion frame 12 into a position when the button 76 is released. For example, the biasing member may be configured to bias the cushion frame 12 toward the face of the patient when the button 76 is pressed. Alternatively, the biasing member may be configured to bias the cushion frame 12 away from the face of the patient when the button 76 is pressed.

The cushions 25 may be supported on the cushion frame 12 by a resilient member 90. For example, the resilient member 90 may be a silicone rubber stem-like member. As the cushion frame 12 rotates about the axis 70, the resilient member 90 is able to flex or bend to maintain the contact face of the cushion 25 flush against the face of the patient, e.g. against the patient's forehead.

It should be appreciated that the auto-adjusting mask stabilizer may be incorporated into any mask system where the fitting and correct adjustment of the mask relative to the wearer's head or face can be achieved. For example, the auto-adjusting mask stabilizer of the invention may be used in mask systems that are not provided with a forehead support, but instead utilize, for example, a cheek support or upper lip support. It should further be appreciated that the auto-adjusting mask stabilizer of the invention may be utilized in a mask system in which the forehead support is located or otherwise attached to a headgear system. It should be even further appreciated that the auto-adjusting mask stabilizer may not include a lock mechanism. In such case, the cushion frame would be biased against the patient's head, e.g., forehead, by the biasing element and its position would self-adjust to the patient.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A forehead support for a facial mask, the mask including a mask frame and a mask cushion attached to the mask frame and adapted to contact a face of a patient in a substantially airtight manner, the forehead support being adapted to be moveable between a first position with respect to the mask frame and a second position with respect to the mask frame, the forehead support comprising:
    a forehead support frame;
    at least one forehead pad attached to the forehead support frame and adapted to contact the patient's forehead when the facial mask is mounted on the patient's face;
    a spring biasing mechanism separate from a headgear and the at least one forehead pad, the spring biasing mechanism being configured to be positioned between the mask frame and the forehead support frame, the spring biasing mechanism being configured so that a spring action of the spring biasing mechanism urges the forehead support toward the second position; and
    a locking mechanism adapted to hold the forehead support in position with respect to the mask frame.

2. The forehead support according to claim 1, wherein the spring biasing mechanism is configured to urge the forehead support against the patient's forehead.

3. The forehead support according to claim 1, further comprising a release mechanism adapted to release the forehead support from a hold position with respect to the mask frame.

4. The forehead support according to claim 1, wherein the forehead support is movable by translation.

5. The forehead support according to claim 1, wherein the forehead support is moveable by rotation.

6. The forehead support according to claim 1, further comprising a second locking mechanism adapted to hold the forehead support in a predetermined orientation with respect to the mask frame.

7. The forehead support according to claim 1, wherein the spring biasing mechanism is configured to urge the forehead support into a stabilizing position on the forehead of the patient.

8. The forehead support according to claim 1, wherein the forehead support includes a housing that at least partially houses the spring biasing mechanism.

9. The forehead support according claim 4, wherein the forehead support is movable by linear translation.

10. The forehead support according to claim 9, wherein the forehead support is movable by horizontal translation.

11. A stabilizer for a patient interface of a CPAP system, the patient interface being adapted to engage a patient's face and including a patient interface frame, the stabilizer being adapted to be moveable between a first position with respect to the patient interface frame and a second position with respect to the patient interface frame, the stabilizer comprising:
    a spring biasing mechanism being separate from a headgear and configured to engage the patient interface frame such that a spring action of the spring biasing mechanism urges the stabilizer from the first position toward the second position; and
    a locking mechanism adapted to hold the stabilizer in at least one intermediate position between the first and the second positions,
    wherein the headgear comprises a strap.

12. The stabilizer according to claim 11, wherein the spring biasing mechanism is a compression spring.

13. The stabilizer according to claim 12, wherein a resistance to a compression of the compression spring generates a biasing force that directs the stabilizer to the second position.

14. A mask assembly comprising:
    a frame,
    a forehead support,
    a spring biasing mechanism, and
    a locking mechanism adapted to lock the spring biasing mechanism in a compressed state;
    wherein the forehead support is free to move between a first position relative to the frame and a second position relative to the frame and the spring biasing mechanism is arranged so that a spring action of the spring biasing mechanism directs the forehead support to the second position.

15. The mask assembly according to claim 14, wherein the spring biasing mechanism is centrally located in the forehead support between headgear connectors.

16. The mask assembly according to claim 14, wherein the spring biasing mechanism is separate from a headgear of the mask assembly.

17. A mask assembly comprising:
    headgear;
    a mask frame;
    a mask cushion attached to the mask frame and adapted to contact a face of a patient in a substantially airtight manner;
    a stabilizing element movably connected to the mask frame;
    a stabilizing element cushion attached to the stabilizing element and adapted to contact a forehead of the patient when the mask assembly engages the patient's face; and
    a spring biasing mechanism separate from the headgear and arranged to exert a first force on the mask frame and a second force on the stabilizing element so that the stabilizing element self-adjusts to align itself in position with respect to the patient when the mask assembly is mounted on the patient's face.

18. The mask assembly of claim 17, wherein the stabilizing element is a forehead support.

19. The mask assembly of claim 18, wherein the forehead support self-adjusts itself with respect to the forehead of the patient.

20. The mask assembly of claim 17, wherein the stabilizing element is resiliently biased.

21. The mask assembly of claim 20, wherein the stabilizing element is configured to be biased to align itself against the skin of the patient when the mask assembly is mounted on the patient's face.

22. The mask assembly of claim 17, further comprising at least one locking mechanism for locking the stabilizing element in position with respect to the mask frame.

23. The mask assembly according to claim 17, wherein the stabilizing element includes a housing that at least partially houses the spring biasing mechanism.

24. A mask assembly, comprising:
    a mask frame;

a cushion attached to the mask frame and adapted to contact the face of a patient in a substantially airtight manner;

a stabilizer element connected to the mask frame and translatably biased via a spring action of a spring biasing element adapted to be compressed between the stabilizer element and the mask frame; and a pad supported by the stabilizer element, the pad being configured to contact the patient's face, wherein the spring biasing element engages the mask frame and an inclination angle between the stabilizer element and the mask frame remains constant as the stabilizer translates with respect to the mask frame.

25. A mask assembly according to claim 24, further comprising a lock mechanism that locks the stabilizer element in position with respect to the mask frame.

26. A mask assembly according to claim 25, wherein the position is one of a plurality of discrete positions.

27. A mask assembly according to claim 25, wherein the position is one of an infinite number of positions.

28. A mask assembly according to claim 25, wherein the stabilizer element includes a shaft translatably supported in a cylindrical extension of the mask frame, and the lock mechanism comprises a pawl on the cylindrical extension that engages the shaft.

29. A mask assembly according to claim 28, wherein the pawl includes ratchet teeth that engage corresponding ratchet teeth formed on the shaft.

30. A mask assembly according to claim 28, wherein the pawl is supported on a cantilevered lever formed in an outer surface of the cylindrical extension.

31. A mask assembly according to claim 28, further comprising a release button formed on the pawl, wherein depressing the release button disengages the pawl from the shaft and releases the lock mechanism.

32. A mask assembly according to claim 25, wherein the stabilizer element includes a shaft translatably supported in a cylindrical extension of the mask frame, and the lock mechanism comprises a radial projection on an inner cylindrical surface of the cylindrical extension that frictionally engages an outer cylindrical surface of the shaft.

33. A mask assembly according to claim 32, further comprising a release mechanism that releases the frictional engagement of the radial projection and the outer cylindrical surface.

34. A mask assembly according to claim 33, wherein the release mechanism comprises a spring biased button that deforms the cylindrical extension when depressed to release the frictional engagement.

35. A mask assembly according to claim 24, wherein the stabilizer element is configured to contact the patient's forehead.

36. A mask assembly according to claim 24, wherein the stabilizer element is configured to contact a cheek of the patient.

37. A mask assembly according to claim 24, wherein the spring biasing element is configured to bias the stabilizer element away from the mask frame.

38. A mask assembly according to claim 37, wherein the spring biasing element comprises a coil spring, an air spring, a foam, or an elastic band.

39. A mask assembly according to claim 29, wherein the ratchet teeth are spaced about 1 mm apart.

40. A mask assembly according to claim 31, further comprising a bushing between the release button and the outer surface of the cylindrical extension.

41. A mask assembly according to claim 28, wherein the shaft comprises grooves in its outer surface that receive corresponding projections on the inner surface of the cylindrical extension.

42. The mask assembly according to claim 24, wherein the stabilizer element includes a housing that at least partially houses the spring biasing element.

43. The mask assembly according to claim 24, further comprising a headgear to support the mask assembly on the patient's head.

44. A stabilizer for a mask assembly, comprising:

a mask frame extension adapted to be connected to a mask frame of the mask assembly;

a pad support element translatably supported by the mask frame extension, the pad support element being configured to support a pad that is adapted to contact a face of a wearer of the mask assembly; and a spring biasing element that is separate from headgear and the pad support element, the spring biasing element engaging the mask frame extension and the pad support element so that a spring action of the spring biasing mechanism biases the pad support element with respect to the mask frame extension, wherein the headgear comprises a strap.

45. A stabilizer according to claim 44, further comprising a lock mechanism that locks the pad support element in position relative to the mask frame extension.

46. A stabilizer according to claim 44, wherein the pad support element supports a forehead pad.

47. A stabilizer according to claim 44, wherein the pad support element supports a cheek pad.

48. A stabilizer according to claim 44, wherein the stabilizer includes a housing that at least partially houses the spring biasing element.

49. A respiratory mask for delivering a flow of breathable gas to a patient, comprising:

a mask frame, the mask frame including a rear side adapted to face the patient when the respiratory mask is mounted on the patient's face and a front side including an aperture for introduction of the flow of breathable gas; and an adjustable forehead support mechanism, the adjustable forehead support mechanism comprising:

a housing provided on the mask frame, the housing having an opening on a rear side of the housing, a forehead support assembly configured to engage the forehead of the patient when the respiratory mask is mounted on the patient's face, the forehead support assembly comprising a rigid shaft extending forwardly from a forehead support assembly frame through the opening, the shaft being movable so that the forehead support assembly frame is movable toward and away from the housing, and an adjustment mechanism configured to adjust a distance of the forehead support assembly from the housing and including a spring biasing mechanism that engages the housing and the forehead support assembly.

50. A respiratory mask according to claim 49, further comprising a sleeve provided in the housing, wherein the opening is provided in the sleeve.

51. A respiratory mask according to claim 50, wherein the shaft has a tubular wall and a longitudinal groove formed in the tubular wall.

52. A respiratory mask according to claim 51, wherein the longitudinal groove comprises a plurality of locking portions and the adjustment mechanism comprises a locking member that extends through the sleeve and engages at least one of the locking portions to lock the forehead support assembly in position relative to the housing.

53. A respiratory mask according to claim 52, wherein the locking member is movable into the sleeve to disengage the locking member from the locking portions so that the locking member is slidable along the longitudinal groove to adjust the distance of the forehead support assembly with respect to the housing.

54. A respiratory mask according to claim 53, wherein the adjustment mechanism further comprises an actuating member connected to the locking member, the actuating member being operable to disengage the locking member from the locking portions of the longitudinal groove.

55. A respiratory mask according to claim 54, wherein the actuating member is operable in a direction transverse to a longitudinal axis of the sleeve.

56. A respiratory mask according to claim 55, wherein the actuating member is connected to the housing.

57. A respiratory mask according to claim 56, wherein the actuating member is resiliently biased into a position in which the locking member is engaged with at least one of the locking portions of the longitudinal groove.

58. A respiratory mask according to claim 49, wherein the adjustment mechanism includes a housing that at least partially houses the spring biasing mechanism.

59. A respiratory mask according to claim 49, wherein the spring biasing mechanism is separate from a headgear of the respiratory mask.

* * * * *